US011369552B1

(12) United States Patent
Komarova

(10) Patent No.: US 11,369,552 B1
(45) Date of Patent: Jun. 28, 2022

(54) AQUEOUS NAIL POLISH REMOVER

(71) Applicant: Elena Yurievna Komarova, Prospect, KY (US)

(72) Inventor: Elena Yurievna Komarova, Prospect, KY (US)

(73) Assignee: Elena Yurievna Komarova, Prospect, KY (US)

( * ) Notice: Subject to any disclaimer, the term of this patent is extended or adjusted under 35 U.S.C. 154(b) by 0 days.

(21) Appl. No.: 17/018,818

(22) Filed: Sep. 11, 2020

(51) Int. Cl.
*A61K 8/42* (2006.01)
*A61K 8/04* (2006.01)
*A61Q 3/04* (2006.01)

(52) U.S. Cl.
CPC .............. *A61K 8/42* (2013.01); *A61K 8/042* (2013.01); *A61Q 3/04* (2013.01); *A61K 2800/28* (2013.01); *A61K 2800/30* (2013.01); *A61K 2800/48* (2013.01)

(58) Field of Classification Search
CPC ...... A61K 8/42; A61K 8/042; A61K 2800/28; A61K 2800/48; A61K 2800/30; A61Q 3/00
See application file for complete search history.

(56) References Cited

U.S. PATENT DOCUMENTS

| | | | |
|---|---|---|---|
| 4,485,037 A | 11/1984 | Curtis | |
| 5,294,435 A | 3/1994 | Remz et al. | |
| 5,344,583 A | 9/1994 | Bayless | |
| 5,372,742 A | 12/1994 | Bayless | |
| 5,582,333 A | 12/1996 | Bennett | |
| 6,028,040 A | 2/2000 | Jarema | |
| 6,348,201 B2 | 2/2002 | Murata et al. | |
| 6,432,421 B1 | 8/2002 | Brown et al. | |
| 6,572,845 B2 | 6/2003 | Ensley | |
| 6,689,727 B1 | 2/2004 | Olsson | |
| 6,998,371 B2 | 2/2006 | Tavares | |
| 7,074,746 B2 | 7/2006 | Fujii | |
| 8,409,552 B2 | 4/2013 | Schmaus et al. | |
| 8,835,369 B2 | 9/2014 | Cifelli | |
| 8,961,680 B2 | 2/2015 | Pasin et al. | |
| 9,399,005 B2 | 7/2016 | Valkonen et al. | |
| 9,931,284 B2 | 4/2018 | Kozacheck et al. | |
| 9,987,212 B2 | 6/2018 | Macneill et al. | |
| 10,085,926 B2 | 10/2018 | Wallach et al. | |
| 10,351,523 B2 | 7/2019 | Nacharaju et al. | |
| 10,494,466 B2 | 12/2019 | Chuang et al. | |
| 10,617,191 B2 | 4/2020 | Zhen | |
| 2014/0309153 A1* | 10/2014 | Valkonen | C11D 3/201 510/118 |
| 2017/0007516 A1 | 1/2017 | Mercado et al. | |
| 2020/0069544 A1 | 3/2020 | Guimont et al. | |

FOREIGN PATENT DOCUMENTS

| | | |
|---|---|---|
| EP | 0009691 | 4/1980 |
| WO | 9850005 | 11/1998 |
| WO | 2009106338 | 9/2009 |

OTHER PUBLICATIONS

Stylecraze ([retrieved from on-line website: https://www.stylecraze.com/articles/how-to-remove-gel-nail-polish-at-home/, published in 2017, pp. 1-17]). (Year: 2017).*

* cited by examiner

*Primary Examiner* — Kyung S Chang
(74) *Attorney, Agent, or Firm* — Middleton Reutlinger

(57) ABSTRACT

An aqueous composition for removing nail polish from a wearer's nail(s) is disclosed. This nail polish remover is essentially free of organic solvents, such as acetone, ethyl acetate, butyl acetate, and the like. The aqueous nail polish remover includes at least one amide of an aminoalcohol at a concentration of about 0.1% or greater in water.

19 Claims, No Drawings

AQUEOUS NAIL POLISH REMOVER

FIELD OF INVENTION

This invention relates to a nail polish remover composition which is essentially free of solvents and consists predominantly of water with ethanolamide-based surfactants. The remover is biodegradable, non-volatile, non-flammable, biodegradable, and non-toxic.

BACKGROUND OF THE INVENTION

Nail polish removers have been researched since nail polish was invented. By saying "nail polish remover" we assume a substance a combination of substances, or mixture that eases the removal of a nail polish from the surface of fingernail or toenail. It is desirable that nail polish be removed from fingernail or toenails without damaging nail surface as well as skin of the person who uses the remover, which may include a wearer and/or nail salon personnel when the removal procedure is performed in a nail salon.

A typical nail polish consists of pigment/pigments dispersed in a film forming polymer or binder. Originally, a nail polish comprised nitrocellulose as a polymeric binder that has very good film forming and pigment wetting properties, pigment(s), pigment dispersing aid/dispersants, surfactants and adhesion improving chemicals.

Relatively recently, acrylic and methacrylic polymers have been utilized as polymeric binders in nail polishes. Even more recently ultraviolent (UV) gel polish was introduced. UV gel nail polish comprises photochemically cross-linked acrylates and methacrylates after the polish is cured under UV or LED light.

In order to remove any polish from the nail(s), the remover usually needs to dissolve or at least partially dissolve or swell the film of nail polish.

Traditional nail polish removers may contain mixtures of organic solvents such as acetone, ethyl acetate, butyl acetate. These organic solvents may be conventionally used because these solvents provide good polish dissolving and removal characteristics.

Other solvents such as propylene carbonate, alcohols, diethers, diesters, esters, carbonate esters, methyl ethyl ketone, benzyl alcohol, parachlorobenzotrifluoride and combinations thereof may have also been utilized in a nail polish remover composition.

All of the aforementioned solvents are flammable and may emit and fill a room with their unhealthy and/or unpleasant odors. These solvents are powerful solvents; they can penetrate the skin easily and may dry the skin upon evaporation. Keratin layers that make the nail can be dried by these solvents as well damage the nail after prolonged use.

There is a need to provide efficient nail polish remover using compositions that are substantially free of harsh solvents. There is a need for a composition completely void of organic solvents.

SUMMARY

The present composition relates to a solvent deficient aqueous solution that consists of mostly water and at least one of the ethanolamine derived surfactants, such as amides. A further aspect of the present composition relates to a solvent deficient nail polish remover as described above optionally further comprising a thickening polymer or clay, optionally at least one other surfactant, optionally colorants such as a dye or a pigment or a combination there of, optionally essential oils or fragrances, and optionally at least one abrasive agent and optionally at least one emollient agent.

In a first aspect, an aqueous composition for nail polish removal described herein includes at least one amide of an aminoalcohol at a concentration of about 0.01% or greater in water, where the composition is essentially free of acetone, ethyl acetate, butyl acetate, and other solvents.

In some embodiments, the at least one amide of an aminoalcohol is an ethanolamide. In some such embodiments, the ethanolamide is a cocamide diethanolamine.

In some embodiments, a user soaks at least one toenail or fingernail in the composition for about 30 seconds to about 20 minutes when the composition is at a temperature of about 20 degrees Celsius to about 45 degrees Celsius. In some such embodiments, the at least one amide of an aminoalcohol is configured to break a bond between nail polish and nail surface, in some embodiments the amide breaks the bond between an acidic adhesion promoter in a nail polish and a surface of the at least one toenail or fingernail.

In some embodiments, the least one amide of an aminoalcohol is at a concentration of about 0.01% to about 50.0% in water.

In some embodiments, the composition further includes at least one thickening agent, where the at least one thickening agent comprises between about 0.05% and about 50% by weight of the composition. In some such embodiments, the at least one thickening agent results in the composition being in a gel form.

In some embodiments, the composition further includes at least one abrasive agent, where the at least one abrasive agent comprises between about 0.5% and about 50% by weight of the composition. In other embodiments, the composition further includes at least one emollient agent, where the at least one emollient agent comprises between about 0.5% and about 60% by weight of the composition. In still other embodiments, the composition further includes at least one fragrance.

In some embodiments, the composition further includes a non-aminoalcohol-based surfactant, where the non-aminoalcohol-based surfactant comprises between about 0.01% and about 30% by weight of the composition.

In another aspect, an aqueous composition for nail polish removal includes an ethanolamide at a concentration of about 0.01% to about 50.0% in water, where the composition is essentially free of acetone, ethyl acetate, and butyl acetate; and where the composition, when in contact with a user's fingernail or toenail, is configured to break a bond between a nail polish and a nail surface. In some embodiments, the ethanolamide may break the bond between an acidic adhesion promoter in a nail polish and a surface of the user's fingernail or toenail.

In some embodiments, the composition further includes at least one thickening agent, where the at least one thickening agent comprises between about 0.05% and about 50% by weight of the composition. In other embodiments, the composition further includes at least one abrasive agent, where the at least one abrasive agent comprises between about 0.5% and about 50% by weight of the composition. In still other embodiments, the composition further includes at least one emollient agent, where the at least one emollient agent comprises between about 0.5% and about 60% by weight of the composition. In still yet other embodiments, the composition further includes a non-aminoalcohol-based surfactant, where the non-aminoalcohol-based surfactant comprises between about 0.01% and about 30% by weight of the composition.

In yet another aspect, a method of removing a nail polish from a wearer's nails includes: obtaining a composition for nail polish removal, the composition including an aminoalcohol at a concentration of about 0.01% or greater in water that is essentially free of acetone, ethyl acetate, butyl acetate and other solvents; soaking at least one toenail or fingernail in the composition for about 30 seconds to about 20 minutes, where the composition is at a temperature of about 20 to about 45 degrees Celsius; where, during soaking, the at least one amide of an aminoalcohol breaks a bond between a nail polish and a nail surface; and removing the nail polish from the surface of the at least one toenail or fingernail.

In some embodiments, removing nail polish from the surface of the at least one toenail or fingernail further includes peeling the nail polish off of the surface of the at least one toenails or fingernails.

In some embodiments, removing nail polish from a wearer's nails, where obtaining a composition for nail polish removal additionally includes obtaining an about 50% PEG-6 cocamide concentrate solution and diluting the about 50% PEG-6 cocamide concentrate solution at about 1:50 with water, thereby forming an about 1% solution.

The following detailed description and examples are explanatory and not restrictive of the embodiments.

DETAILED DESCRIPTION

Definitions of the terms and chemical names employed in the description of the present invention:

An "ethanolamine" refers to a mono-ethanolamine, diethanolamine or triethanolamine. Additionally, "ethanolamine" encompasses mono- or dialkyl ethanolamine such as, for example, dimethylthanolamine. The structures are shown in the Structure 1. Other amines that can be safely utilized in cosmetic compositions are included in these embodiments.

Structure 1, below, illustrates structures of: (a) monoethanolamine; (b) diethanolamine: (c) triethanolamine; (d) mono- of dialkyl ethanolamine; In each of these structures, R can be —H or any alkyl.

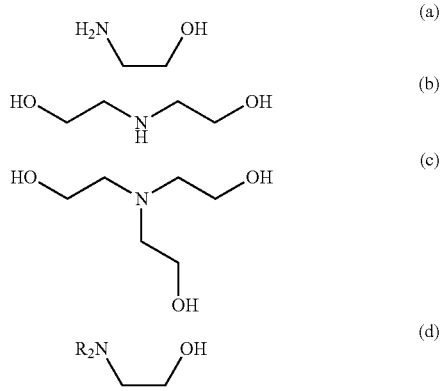

The term "at least one" as used herein mean one or more, therefore, it may mean one individual component or the combinations of components.

The term "solvent" as used herein refers to an organic solvent, a compound consisting of carbon, hydrogen, oxygen, nitrogen and sulfur in its structure. Some examples of such solvents include, but are not limited to: acetone, butyl acetate, ethyl acetate, methyl ethyl ketone, n-methyl-pyrrolidone, propylene carbonate, esters, alcohols, diethers, diesters, carbonate esters, methyl ethyl ketone, benzyl alcohol, parachlorobenzotrifluoride, etc.

The terms "solvent deficient" or "essentially free of solvent" as used herein refers to a solution preferably without any amount of solvent(s) present in the composition, but it is possible that a small amount of solvent may be present in the composition. "Solvent deficient" or "essentially free of solvent" means that the aqueous composition contains less than 3% of any solvent, in the preferred embodiment the composition contains less than 1% of any solvent, in the most preferred embodiment the aqueous composition contains no solvent (0%).

The term "surfactant" as used herein refers to a chemical compound that when dissolved in water reduces it surface tension thus facilitating dispersion of water-insoluble compounds such as oils in water.

The term "abrasive" as used herein refers to an agent/material that can cause removal of surface of another material by rubbing or grinding, or otherwise being able to abrade.

The term "emollient" as used herein refers to an additive that softens the skin.

The term "Hazardous Air Pollutants" (HAP), as used herein refers to toxic air pollutants or air toxics, are those pollutants that are known or suspected to cause cancer or other serious health effects, such as reproductive effects or birth defects, or adverse environmental effects.

The term "thickening agent" as used herein refers to a clay, polymeric thickener, or inorganic clay that helps to increase viscosity or create a loose or a strong gel.

A composition and process for removing nail polish from a surface such as a human fingernail or toenail is described. As used herein, the term "nail polish" refers generally to any cosmetic composition that may be applied to a fingernail or a toenail and these compositions include a variety of polishes that are present on the market today such as UV gel polish, acrylic gel, water-based nail enamels, regular solvent-borne nail polish, spray nail polish, etc., and the like.

The nail polish remover composition comprises water and an ethanolamine-based surfactant that includes, but is not limited to, ethanolamide-based surfactants. Ethanol amides include the product of reaction of various saturated and unsaturated acids with mono-, di- or triethanolamine and other ethanolamine derivatives including but not limited to mono-, di- or tri-ehtanolamines as well. Saturated or unsaturated, as used in this context, indicates organic compounds that comprise of hydrocarbons. The main difference between saturated and unsaturated compounds is that saturated compounds have only carbon-carbon single bonds whereas unsaturated compounds have carbon-carbon double bonds and triple bonds.

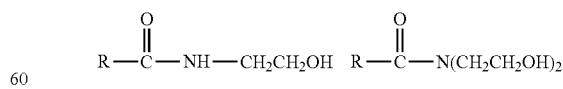

Structure 2.

Structure 2 illustrates various structures of ehtanolamides, where R may have any structure.

Other amide-based surfactants and compounds, as well as compounds based on ethanolamines are within by the scope of this disclosure.

Amides of other aminoalcohols such as shown in Structure 3, below, where R can have any structure and n can be any number. Specially, Structure 3 illustrates the general structure of other amides included within the scope of this disclosure.

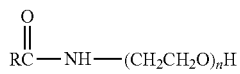

Structure 3.

Ethanolamide of inorganic acids such as phosphoric, carbonic and other acids known to the skilled in the art are included in the scope of this disclosure as well. Any product of the reaction of ethanolamine with any acid that can be added to water to remove nail polish without damaging the skin or nail are considered embodiments of the present disclosure.

Ethanolamide (or any amide) surfactant may help break a bond between a nail polish and a nail surface. In some instances, this bond is the bond between an acidic adhesion promoter in the nail polish and the nail surface. This process detaches the polish from the surface of the nail without affecting the surface of the nail, cuticle of the nail, or skin around the nail adversely. Most conventional nail polish compositions rely on acidic adhesion promoters to better attach the polish to the nail surface in order to prevent premature peeling or chipping of the polish from the nail. The ethanolamine-based compounds described herein break that bond by neutralizing the adhesion promoter and releasing it form the nail surface without damaging the nail.

In accordance with the present embodiment, compositions for removing nail polish may comprise at least 0.01% of at least one ethanolamide in water are provided.

A further aspect of the present embodiment relates to a solvent-deficient nail polish remover as described above may optionally include a thickening polymer or clay, optionally at least one other surfactant, optionally colorants such as a dye or a pigment or a combination thereof, optionally essential oils or fragrances, and optionally at least one abrasive agent and optionally at least one emollient agent.

The thickener can be chosen from a non-limiting list of thickening agents that can be used according to various embodiments. The list of thickening agents includes those conventionally used in cosmetics, such as polymers of natural origin, synthetic polymers. Non-ionic, anionic, cationic, amphiphilic, and amphoteric polymers, and other known rheology modifiers, such as clays and other inorganic thickeners allowed for use in cosmetics. Some examples of the thickeners may include, but not limited, to natural waxes, and gums, starch, synthetic polymers, emulsifying thickeners including polysaccharides, proteins, alcohols, silicones, and the like.

The at least one thickener may be present in the compositions described herein in an amount greater than 0.05% and less than 50%, by weight of the composition.

In some instances, non-ethanolamide-based surfactants may optionally be present in the composition described herein. Such surfactants can be chosen from a non-limiting list of the surfactants allowed in cosmetics. The list comprises anionic, cationic and non-ionic types of surfactants.

The non-ethanolamide-based surfactant may be present in the compositions described herein in an amount greater than 0.01% and less than 30%, by weight of the composition.

An abrasive agent may also be added to the solvent-deficient composition presented herein. The compositions comprising at least one abrasive agent or scrubbing compound, are described. An abrasive agent or scrubbing compound is an agent or an additive providing mechanical exfoliation, and in accordance with the composition described herein may be chosen from the following non-limiting list of abrasive agents: silica, alumina, perlite, pumice, sodium bicarbonate, polylactic acid particles, polyethylene, polypropylene, polyethylene terephthalate, polyacrylate, polymethacrylate, polyamide, or polyurethane particles, as well as other natural scrubbing compounds made with ground coffee beans, ground nut shells, coconut husk, apricot kernel, and soft waxes like carnauba jojoba.

The abrasive agent may be present in the composition of the aqueous solvent-deficient remover in a weight concentration greater than 0.5% and less than 50%, by weight.

An emollient agent may be chosen form a non-limiting list of cosmetically approved emollients such as glycerol, lanolin, mineral oil, White Soft Paraffin, castor oil, cetyl alcohol, cetearyl alcohol, cocoa butter, isopropyl myristate, isopropyl palmitate, liquid paraffin, polyethylene glycols, shea butter, silicone oils, stearic acid, and stearyl alcohol.

An emollient agent may be present in the aqueous nail polish remover compositions in concentrations greater than 0.5% and less than 60%, by weight.

Auxiliaries/Additives

The aforementioned compositions may additionally comprise an additive or auxiliary component commonly used in cosmetic compositions. A person skilled in the art would be able to incorporate such additives/auxiliaries known in the industry into a nail polish remover composition. These additives can be chosen from, but not limited to, such common additives to a cosmetic composition as: biocides, preservatives, fragrances, oils, waxes, antioxidants, dispersing agents, wetting agents, defoaming agents, neutralizing agents, moisturizing agents, stabilizing agents, vitamins, proteins, ceramides, plant extracts, fibers, and the like, and their mixtures. These additives may be present in the composition described herein in a percentage from 0% to 40%, by weight.

All compositions described herein may be cosmetically or dermatologically acceptable, and consist of non-toxic physiologically acceptable ingredients.

Other embodiments include methods of removing nail polish from nails. These include the application of a nail polish remover composition to the nails onto which a nail polish has been previously been applied. Specifically, for fingernails the hands may be soaked in the nail polish remover composition. This application/soaking may result not only in the removal of the nail polish, but also may result in softened and moisturized skin.

The composition described herein is water miscible and water-soluble. The composition can also be rinsed from hands and nails with water, or with water and soap.

All numerical ranges and parameters setting forth the broad scope of the invention are approximations. When used in this specification and the claims as an adverb rather than a preposition, "about" means "approximately" and comprises the stated value and every value within 10% of that value; in other words, "about 100%" includes 90% and 110% and every value in between.

The following examples are intended to illustrate the invention without limiting the scope of discovery as a result. All percentages listed are by weight unless otherwise noted.

EXAMPLES

Example 1—Procedure for Preparation of the Aqueous Remover

Most of ethanolamides are miscible with water or soluble in water to some extent. The preparation of the aqueous remover includes mixing/stirring of the ethanol amide into water at a certain concentration. Occasionally, this preparation may also require heating to about 50-60° C. and stirring.

TABLE 1

| Ethanolamide Surfactant | Physical State (at RT) | Concentration range (%) | Temperature to dissolve (° C.) | Solution Description |
|---|---|---|---|---|
| Ninol ® C-5 (Stepan) | Liquid | Miscible with water at any ratios | Ambient temperature | True solution |
| Ninol ® CMP (Stepan) | Solid | 0-2 | 60 | Cloudy solution |
| Ninol ® COMF-N (Stepan) | Solid | 0-3 | 60 | Cloudy solution |
| Dimethylethanolamine (Huntsman) | Liquid | Miscible with water at any ratios | Ambient temperature | True Solution |

Example 2—Methods for Nail Polish Removal with Aqueous Nail Polish Remover

There may be multiple methods for removing nail polish using the aqueous nail polish removers described herein. First, a user may soak the polished fingers in aqueous polish remover for 5 min at any temperature between about 20° C. and 45° C. A user may then push away or peel off the nail polish from the nail as required. In some instances, the nail polish may detach on its own after soaking.

A second method of removing nail polish using the described compositions may be to apply a gel of aqueous nail polish remover, for example a composition with a quantity of thickener to generate a gel consistency, onto the nail surface. After application of the gel composition, the user may wait for about 5 minutes and remove the polish by pushing it away or peeling it off of the nail. In some instances, the nail polish may detach on its own.

A third method of removing nail polish using the described compositions may include a user soaking their hands in an aqueous nail polish remover solution, as described herein, where the composition may further contain essential oils and emollients. The user may soak their polished hands for several minutes, for example about five (5) to about 10 minutes. After soaking, the nail polish may detach from the nail surface. In some instances, some peeling of the nail polish may be required.

Example 3—Removal of Different Brands of Nail Polish with the Aqueous Nail Polish Remover A variety of commercially available brands of nail polish were tested with the aqueous nail polish remover composition described herein. Each brand was applied to a human nail(s) according to the manufacturer's instructions and was worn for at least three (3) days. After three days, removal of nail polish was attempted using various concentrations of the composition described herein. The condition, results, and details regarding the same are presented in Table 2.

The following nail polishes were utilized in this experiment. The conditions for the application of each polish is also described herein.

CND™ Shellac™ UV gel polish was tested. The base coat was cured for 30 seconds under UV LED. Two color layers (color: BEAU) were applied and cured for 60 seconds under UV LED. Finally, a top coat was applied and cured for 60 seconds. The sticky layer was then removed with rubbing alcohol.

Gelish® soak off gel polish was tested. The foundation was applied and cured for 30 seconds under UV LED light. Two color layers of the gel polish (color Elite 99) were applied and cured under UV LED for 60 seconds per layer. One layer of the "Top It Off" (top coat) was applied and cured under UV LED light for 60 seconds. The sticky inhibition layer was removed with rubbing alcohol.

Essie® regular nail polish was also tested. Two coats of the Essie® (color: signature smile, #230) polish were applied. Both coats were air dried for 10 minutes. This was followed by the application of an Essie top coat (#00) was applied once and air dried for 15 min.

Aquapeel® nail polish was also tested. This nail polish is a UV gel that is specifically formulated to be able to be removed via extended soaking in water. One coat of the base coat was applied. Two coats of the color polish (color: Vanilla Macaron) was applied and followed by one layer of top coat. Each layer was cured under UV LED light for one minute prior to application of the next layer.

The Ninol® CMP aqueous solution of Example 1 was used for the following experiments. The results, conditions, and notes regarding the removal for each polish are provided in Table 2, below.

TABLE 2

Nail polish removal with aqueous solvent deficient remover.

| Nail Polish | Temperature of Water | Soak Time | Details of Removal | Nail Surface After Removal |
|---|---|---|---|---|
| CND ™ Shellac ™ | 98° F. | 3 min. | The nail polish removes in one piece, needed to peel off, detaches easily | Nail surface is smooth: no rough, flaked or scratched patches on the nail surface |
| Essiee ® | 98° F. | 0.5 min. | The nail polish became soft gel-like, once touches, shrinks off the surface of the nail and removes easily | Nail surface is smooth: no rough, flaked or scratched patches on the nail surface |
| Gelish ® | 98° F. | 2 min. | The nail polish removes in one piece, effortlessly peels off, detaches easily | Nail surface is smooth: no rough, flaked or scratched patches on the nail surface |
| Aquapeel ® | 98° F. | 1 min. | The nail polish removes in one piece, no effort is needed to peel, detached easily | Nail surface is smooth: no rough, flaked or scratched patches on the nail surface |

Example 4—Concentration of Aqueous Nail Polish Remover

The effect of the concentration of the ethanolamide on the ease of polish removal and the effect on the condition of the nail surface following polish removal was examined. The test was conducted at room temperature (e.g. the composition was not heated or cooled), using water or the aqueous remover composition described herein. The concentration of Ninol® C-5 (Stepan) was varied from 0% (e.g. water only) to 10% aqueous solution. CND UV gel nail polish (CND™ Shellac™) from Example 3 was utilized in this experiment. The UV gel polish application was applied to the nail(s) as described in Example 3. Table 3, below, provides the results of the tests of various concentrations.

TABLE 3

| Concentration (%) | Soak Time (at 25° C.) in minutes | Removal process and condition of nail surface after removal |
| --- | --- | --- |
| 0 (water only) | 3 | The nail polish detaches from the nail surface with difficulty leaves nails roughened |
| 0.01 | 3 | The nail polish detaches from the nail surface with little effort, some nail damage occurs |
| 0.1 | 3 | The nail polish detaches from nails surface easily, almost no damage to the nail surface |
| 0.5 | 3 | The nail polish detaches very easily from the nail surface, no damage to the nail surface |
| 2 | 3 | The nail polish detaches very easily from the nail surface, no damage to the nail surface |
| 5 and up | 3 | The nail polish detaches very easily from the nail surface, no damage to the nail surface |

Example 5—Preparation of Nail Polish Remover from Concentrate

In some instances, it may be desirable to prepare polish from a pre-dissolved concentrate of an ethanolamides. As an example, a PEG-6 Cocamide (Ninol® C-5 (Stepan)) concentrate with general structure shown in Structure 4, below, may be used.

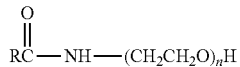

R=Coco
n=average value of 6
Structure 4. PEG-6 COCAMIDE, PEG=polyethiylene glycol PEG-6 cocamide concentrate may be used to prepare the aqueous solution for nail polish removal. For example, a 50% solution of PEG-6 Cocamide is easily miscible with water and may be used as a delivery method.

In some instance, the 50% PEG-6 Cocamide concentrate may be diluted 1:50 with water to make 1% solution suitable for use as a nail polish remover. This dilution may be performed either before commercial sale, as described in Example 7; or, alternatively the concentrate may be sold and diluted by an end-user, for example at home.

Example 6—Removal of Nail Polish with Undiluted Solution

An undiluted PEG-6 COCAMIDE, such as Ninol® C-5 (Stepan) (see Example 5) may be applied directly to nail polish. After this application, the nail(s) may be immersed and soaked in warm water or a moisturizing lotion solution. The nail(s) may be soaked in the warm water or moisturizing lotion solution for about 30 seconds to about 20 minutes. The removal process may be kept at a comfortable temperature by keeping hands in electrically heated mittens or gloves for paraffin hand wax treatment or nail art manicure warmer mittens.

Example 7

In some instances, a user may prefer to use a ready-made solution that does not require measuring and diluting of a solution. In such an instance, the solution may be formulated as described in this Example and then provdied to an end-user. Table 4, below, provides the components that may be provided in such a solution.

TABLE 4

| Component | Percentage (by weight) |
| --- | --- |
| Water | 98.8 |
| PEG-6 COCAMIDE | 1 |
| Benzalkonium Chloride | 0.2 |

This ready-to-use nail polish remover is a 1% solution of a PEG-6 Cocoamide, such as Ninol® C-5 (Stepan), and is prepared by mixing with the appropriate amount of PEG-6 Cocamide with water. For example, the nail polish remover may be prepared through the method described in Example 5.

In some instances, the removal of the nail polish may be more efficient when the diluted aqueous nail polish remover described in Examples 5 and 6 is warmed. A microwave, wax warmer, or the like may be used to heat the nail polish remover solution to a warm, but comfortable temperature (e.g. about 20 degrees Celsius to about 45 degrees Celsius).

It will be appreciated that various additional modifications may be made to the embodiments discussed herein, and that a number of the concepts disclosed herein may be used in combination with one another or may be used separately. Therefore, the invention lies in the claims hereinafter appended. Furthermore, when used in this specification and the claims as an adverb rather than a preposition, "about" means "approximately" and comprises the stated value and every value within 10% of that value; in other words, "about 100%" includes 90% and 110% and every value in between.

What is claimed is:

1. An aqueous composition for nail polish removal comprising at least one amide of an aminoalcohol at a concentration of about 0.01% to about 50% in water, wherein the composition is essentially free of solvents other than the water, acetone, ethyl acetate, butyl acetate, methyl ethyl ketone, n-methyl-pyrrolidone, propylene carbonate, alcohols, diethers, esters, diesters, carbonate esters, methyl ethyl ketone, benzyl alcohol, and parachlorobenzotrifluoride.

2. The aqueous composition for nail polish removal of claim 1, wherein the at least one amide of an aminoalcohol is an ethanolamide.

3. The aqueous composition for nail polish removal of claim 2, wherein the ethanolamide is a cocamide diethanolamine.

4. The aqueous composition for nail polish removal of claim 1, wherein a user soaks at least one toenail or fingernail in the composition for about 30 seconds to about 20 minutes, wherein the composition is at a temperature of about 20 degrees Celsius to about 45 degrees Celsius.

5. The aqueous composition for nail polish removal of claim 4, wherein the at least one amide of an aminoalcohol is configured to break a bond between a nail polish and a surface of the at least one toenail or fingernail.

6. The aqueous composition for nail polish removal of claim 1, wherein the composition further includes at least one thickening agent, wherein the at least one thickening agent comprises between about 0.05% and about 50% by weight of the composition.

7. The aqueous composition for nail polish removal of claim 6, wherein the at least one thickening agent results in the composition being in a gel form.

8. The aqueous composition for nail polish removal of claim 1, wherein the composition further includes at least one abrasive agent, wherein the at least one abrasive agent comprises between about 0.5% and about 50% by weight of the composition.

9. The aqueous composition for nail polish removal of claim 1, wherein the composition further includes at least one emollient agent, wherein the at least one emollient agent comprises between about 0.5% and about 60% by weight of the composition.

10. The aqueous composition for nail polish removal of claim 1, wherein the composition further includes at least one fragrance.

11. The aqueous composition for nail polish removal of claim 1, wherein the composition further includes a non-aminoalcohol-based surfactant, wherein the non-aminoalcohol-based surfactant comprises between about 0.01% and about 30% by weight of the composition.

12. An aqueous composition for nail polish removal comprising an ethanolamide at a concentration of about 0.01% to about 50.0% in water, wherein the composition is essentially free of solvents other than the water, acetone, ethyl acetate, and butyl acetate, methyl ethyl ketone, esters, n-methyl-pyrrolidone, propylene carbonate, alcohols, diethers, diesters, carbonate esters, methyl ethyl ketone, benzyl alcohol, and parachlorobenzotrifluoride;
wherein the composition, when in contact with a user's fingernail or toenail, is configured to break a bond between a nail polish and a surface of the user's fingernail or toenail without damage to the surface of the user's fingernail or toenail.

13. The aqueous composition for nail polish removal of claim 12, wherein the composition further includes at least one thickening agent, wherein the at least one thickening agent comprises between about 0.05% and about 50% by weight of the composition.

14. The aqueous composition for nail polish removal of claim 12, wherein the composition further includes at least one abrasive agent, wherein the at least one abrasive agent comprises between about 0.5% and about 50% by weight of the composition.

15. The aqueous composition for nail polish removal of claim 12, wherein the composition further includes at least one emollient agent, wherein the at least one emollient agent comprises between about 0.5% and about 60% by weight of the composition.

16. The aqueous composition for nail polish removal of claim 12, wherein the composition further includes a non-aminoalcohol-based surfactant, wherein the non-aminoalcohol-based surfactant comprises between about 0.01% and about 30% by weight of the composition.

17. A method of removing a nail polish from a wearer's nails, the method comprising:
obtaining a composition for nail polish removal, the composition including an aminoalcohol at a concentration of about 0.01% to about 50% in water that is essentially free of solvents other than the water, acetone, ethyl acetate, and butyl acetate, methyl ethyl ketone, n-methyl-pyrrolidone, propylene carbonate, alcohols, diethers, esters, diesters, carbonate esters, methyl ethyl ketone, benzyl alcohol, and parachlorobenzotrifluoride;
soaking at least one toenail or fingernail in the composition for about 30 seconds to about 20 minutes, wherein the composition is at a temperature of about 20 to about 45 degrees Celsius;
wherein, during soaking, an at least one amide of an aminoalcohol breaks a bond between a nail polish and a surface of the at least one toenail or fingernail; and
removing the nail polish from the surface of the at least one toenail or fingernail without damage to the surface of the at least one fingernail or toenail.

18. The method of removing nail polish from a wearer's nails of claim 17, wherein removing nail polish from the surface of the at least one toenail or fingernail further includes peeling the nail polish off of the surface of the at least one toenail or fingernail.

19. The method of removing nail polish from a wearer's nails of claim 17, wherein obtaining the composition for nail polish removal further includes:
obtaining an about 50% PEG-6 cocamide concentrate solution; and
diluting the about 50% PEG-6 cocamide concentrate solution at about 1:50 with water, thereby forming an about 1% solution.

* * * * *